United States Patent
Kovach et al.

(10) Patent No.: US 11,918,856 B2
(45) Date of Patent: *Mar. 5, 2024

(54) SYSTEM AND METHOD FOR ESTIMATING MOVEMENT VARIABLES

(71) Applicant: Under Armour, Inc., Baltimore, MD (US)

(72) Inventors: F. Grant Kovach, Baltimore, MD (US); Michael Mazzoleni, Baltimore, MD (US); Jeffrey Allen, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/881,931

(22) Filed: Aug. 5, 2022

(65) Prior Publication Data

US 2022/0370852 A1 Nov. 24, 2022

Related U.S. Application Data

(63) Continuation of application No. 16/259,416, filed on Jan. 28, 2019, now Pat. No. 11,413,500.
(Continued)

(51) Int. Cl.
*A63B 24/00* (2006.01)
*A63B 71/06* (2006.01)
(Continued)

(52) U.S. Cl.
CPC ...... *A63B 24/0062* (2013.01); *A63B 24/0003* (2013.01); *G06V 40/25* (2022.01);
(Continued)

(58) Field of Classification Search
CPC ............ A63B 24/0062; A63B 24/0003; A63B 2071/0663; A63B 2220/12;
(Continued)

(56) References Cited

U.S. PATENT DOCUMENTS 6,356,856 B1 3/2002 Damen et al.
10,216,985 B2 * 2/2019 White .................... G06V 40/25
(Continued)

*Primary Examiner* — Pierre E Elisca
(74) *Attorney, Agent, or Firm* — Maginot, Moore & Beck, LLP

(57) ABSTRACT

A fitness tracking system for generating movement variables corresponding to movement of a user includes a monitoring device, a personal electronic device, and a remote processing server. The monitoring device is configured to be worn or carried by the user and includes a movement sensor configured to collect movement data. The personal electronic device is operably connected to the monitoring device. At least one of the personal electronic device and the monitoring device is configured to calculate feature data by applying a set of rules to the movement data, to calculate raw speed data corresponding to a speed of the user from the subset of the movement data, and to calculate raw distance data corresponding to a distance moved by the user from the subset of the movement data. The remote processing server includes a machine learning model for processing at least the feature data.

21 Claims, 9 Drawing Sheets

Related U.S. Application Data

(60) Provisional application No. 62/624,214, filed on Jan. 31, 2018.

(51) Int. Cl.
  *G01C 22/00* (2006.01)
  *G06V 40/20* (2022.01)
  *G16H 10/60* (2018.01)
  *G16H 20/30* (2018.01)
  *G16H 40/63* (2018.01)
  *G16H 40/67* (2018.01)
  *G16H 50/70* (2018.01)
  *G16H 80/00* (2018.01)

(52) U.S. Cl.
  CPC ............ *G16H 20/30* (2018.01); *G16H 40/63* (2018.01); *G16H 40/67* (2018.01); *G16H 50/70* (2018.01); *A63B 2071/0663* (2013.01); *A63B 2220/12* (2013.01); *A63B 2220/22* (2013.01); *G01C 22/006* (2013.01); *G16H 10/60* (2018.01); *G16H 80/00* (2018.01)

(58) Field of Classification Search
  CPC .... A63B 2220/22; G06V 40/25; G16H 20/30; G16H 40/67; G16H 40/63; G16H 50/70; G16H 10/60; G16H 80/00; G01C 22/006; G06F 18/2135; G06F 2218/08
  USPC .......................................................... 706/15
  See application file for complete search history.

(56) References Cited

U.S. PATENT DOCUMENTS

| | | | |
|---|---|---|---|
| 10,803,305 B2* | 10/2020 | White | G16H 20/30 |
| 11,128,636 B1* | 9/2021 | Jorasch | G07C 9/257 |
| 2013/0171599 A1* | 7/2013 | Bleich | A63B 24/0062 |
| | | | 434/247 |
| 2017/0262699 A1* | 9/2017 | White | A61B 5/7435 |

* cited by examiner

SYSTEM AND METHOD FOR ESTIMATING MOVEMENT VARIABLES

CROSS-REFERENCE TO RELATED APPLICATIONS

This application is a continuation of and claims priority to U.S. patent application Ser. No. 16/259,416, filed Jan. 28, 2019, now U.S. Pat. No. 11,413,500, which application claims priority to U.S. Provisional Patent Application Ser. No. 62/624,214, filed Jan. 31, 2018, the entire contents of which are incorporated herein by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The methods and systems disclosed in this document relate to the field of fitness tracking systems for monitoring user activity and, in particular, to determining movement variables associated with a user of a fitness tracking system.

BACKGROUND

Active individuals, such as walkers, runners, and other athletes commonly use fitness tracking systems to track exercise metrics such as average speed and distance traversed during an exercise session. One type of fitness tracking system includes an accelerometer that collects data used to determine the exercise metrics. In order to improve the user experience of fitness tracking systems, it is desirable to increase the accuracy of the fitness tracking system and associated metrics. Accordingly, improvements in fitness tracking systems are desirable.

SUMMARY

In accordance with one exemplary embodiment of the disclosure, a fitness tracking system for generating at least one movement variable corresponding to movement of a user is disclosed. The fitness tracking system includes a remote processing server in communication with a personal electronic device. The remote processing server is configured to receive from the personal electronic device movement data corresponding to movement of a user, raw speed data corresponding to a speed of the user, raw distance data corresponding to a distance moved by the user, and feature data calculated by applying a set of rules to the movement data. The remote processing server is further configured to apply a machine learning model to the feature data, the raw speed data, and the raw distance data to determine movement variable data corresponding to the at least one movement variable. The at least one movement variable comprises at least one of an estimated speed of the user, an estimated distance moved by the user, and an estimated stride length of the user. The remote processing service is further configured to transmit to the personal electronic device the at least one movement variable determined by the machine learning model of the remote processing server.

Pursuant to another exemplary embodiment of the disclosure, a method of operating a fitness tracking system by determining at least one movement variable corresponding to movement of a user is disclosed. The method includes receiving data from a personal electronic device, wherein the received data includes feature data calculated by applying a set of rules to movement data for the user, raw speed data corresponding to a speed of the user, and raw distance data corresponding to a distance moved by the user. The method further includes applying at least the feature data, the raw speed data, and the raw distance data to a machine learning model at a remote processing server to determine movement variable data corresponding to the at least one movement variable. The at least one movement variable includes at least one of an estimated speed of the user, an estimated distance moved by the user, and an estimated stride length of the user. The method further includes transmitting the movement variable data to a personal electronic device with the remote processing server.

In accordance with yet another exemplary embodiment, a method is disclosed for calculating at least one of a speed of a user and a distance traversed by a user with a fitness tracking system. The method includes collecting movement data corresponding to movement of the user at a personal electronic device worn or carried by the user, and calculating feature data by applying a set of rules to at least a subset of the movement data collected by the personal electronic device. The method further includes wirelessly transmitting the feature data from the personal electronic device to a remote processing server, wherein the remote processing server comprises a machine learning model. Additionally, the method includes receiving, at the personal electronic device, movement variable data from the remote processing server, the movement variable data calculated by the machine learning model based on the feature data and corresponding to the at least one movement variable, the at least one movement variable including at least one of the speed of the user and the distance traversed by the user. Thereafter, the method includes displaying a visual representation of the movement variable data on the display unit of the personal electronic device.

These and other aspects shall become apparent when considered in light of the disclosure provided herein.

BRIEF DESCRIPTION OF THE FIGURES

The foregoing aspects and other features of a fitness tracking system are explained in the following description, taken in connection with the accompanying drawings.

Figure 1:
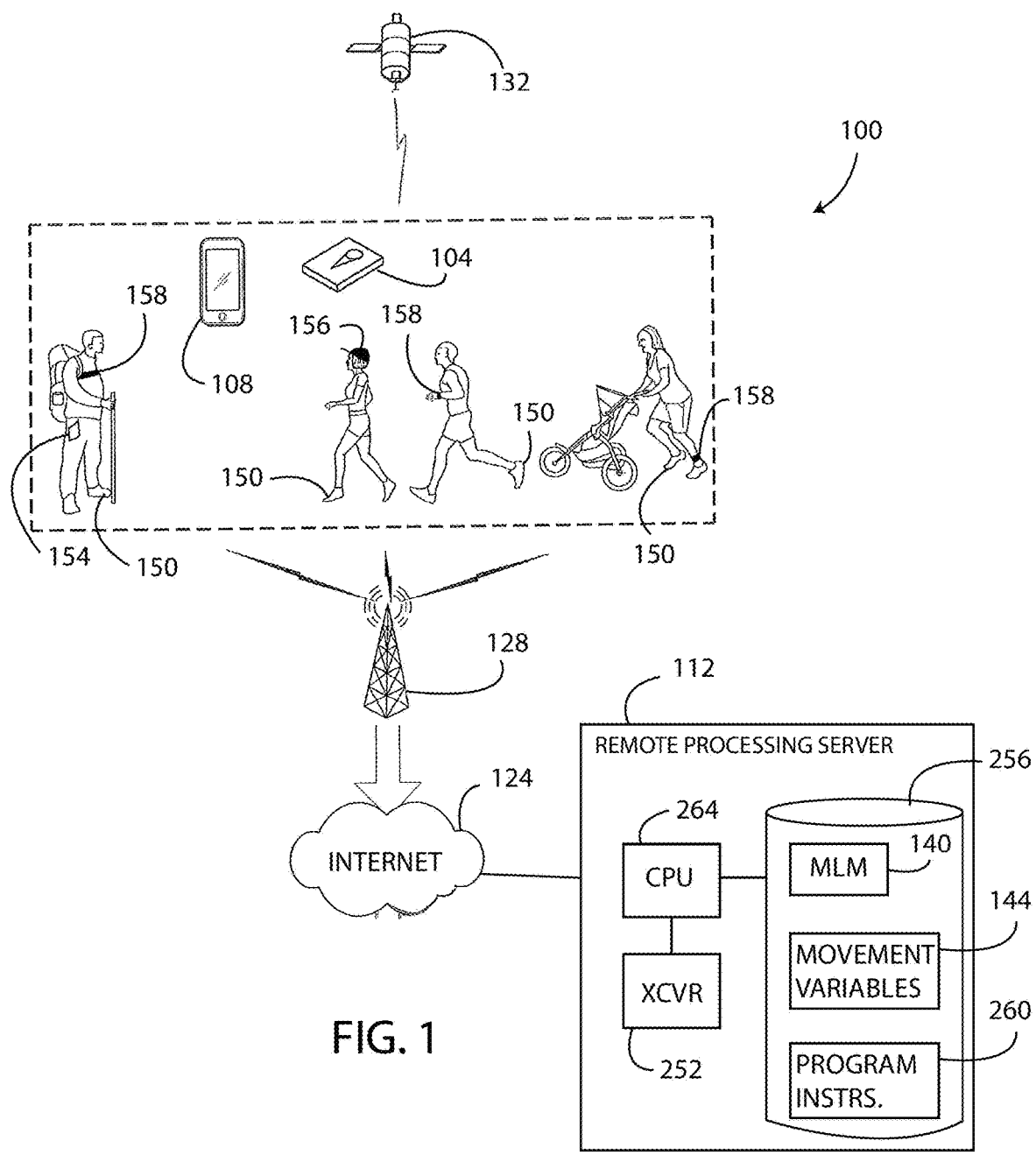
FIG. 1 is a diagram illustrating a fitness tracking system, as disclosed herein.

All Figures © Under Armour, Inc. 2018. All rights reserved.

DETAILED DESCRIPTION

Disclosed embodiments include systems, apparatus, methods, and storage medium associated for generating at least one movement variable corresponding to a movement of a user, and, in particular, for generating at least one movement variable using a machine learning model.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment," "an embodiment," "an exemplary embodiment," and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, operations described may be performed in a different order than the described embodiments. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

As shown in FIG. 1, a fitness tracking system 100 includes a monitoring device 104, a personal electronic device 108, and a remote processing server 112. The fitness tracking system 100 transmits and receives data over the Internet 124 using a cellular network 128, for example. The fitness tracking system 100 may also be configured for use with a global positioning system ("GPS") 132. As disclosed herein, the fitness tracking system 100 collects movement data 136 (FIG. 2) with the monitoring device 104 while the user exercises. At least one of the personal electronic device 108 and the monitoring device 104 calculates feature data 138 (FIG. 3) based on the movement data 136. The feature data 138 is remotely processed by a machine learning model 140 stored on the remote processing server 112 to determine movement variable data 144 based on movements of the user. Exemplary movement variables of the movement variable data 144 include estimated speed, distance, and stride length of the user. The machine learning model 140 increases the accuracy of the determined movement variables, as compared to known approaches for determining the movement variables. Each component of the fitness tracking system 100 and method for operating the fitness tracking system 100 are described herein.

The monitoring device 104 is configured to be worn or carried by a user of the fitness tracking system 100. In one embodiment, the monitoring device 104 is permanently embedded in the sole of a shoe 150 worn by the user, such that the monitoring device 104 cannot be removed from the shoe 150 without destroying the shoe 150. The monitoring device 104 may also be configured for placement in the shoe 150, may be attached to the shoe 150, may be carried in a pocket 154 of the user's clothing, may be attached to a hat 156 worn by the user, and/or may be attached to any portion of the user or the user's clothing or accessories (e.g., wrist band, eyeglasses, necklace, visor, etc.). Moreover, in some embodiments, a left monitoring device 104 is located and/or affixed to the user's left shoe 150 and a right monitoring device 104 is located and/or affixed to the user's right shoe 150; both monitoring devices 104 being configured substantially identically.

In other embodiments, the monitoring device 104 includes a strap 158 to mount the monitoring device 104 onto the user. In this embodiment, the monitoring device 104 may be strapped to the user's wrist, arm, ankle, or chest, for example. In at least one embodiment, the strap 158 and the monitoring device 104 are provided as a watch or a watch-like electronic device. In a further embodiment, the monitoring device 104 is included in a heartrate monitoring device (not shown) that is worn around the wrist, chest, or other body location that is typically used to measure heartrate. Thus, the monitoring device 104 is configured for mounting (permanently or removably) on any element of the user or the user's clothing, footwear, or other article of apparel using any of various mounting means such as adhesives, stitching, pockets, or any of various other mounting means. The monitoring device 104 is located proximate to the user during activities and exercise sessions such as hiking, running, jogging, walking, and the like; whereas the personal electronic device 108 may be left behind or remote to the user during an exercise session. In a further embodiment, which is discussed in greater detail at FIG. 8, the components of the monitoring device 104 are included as part of the personal electronic device 108.

Figure 2:
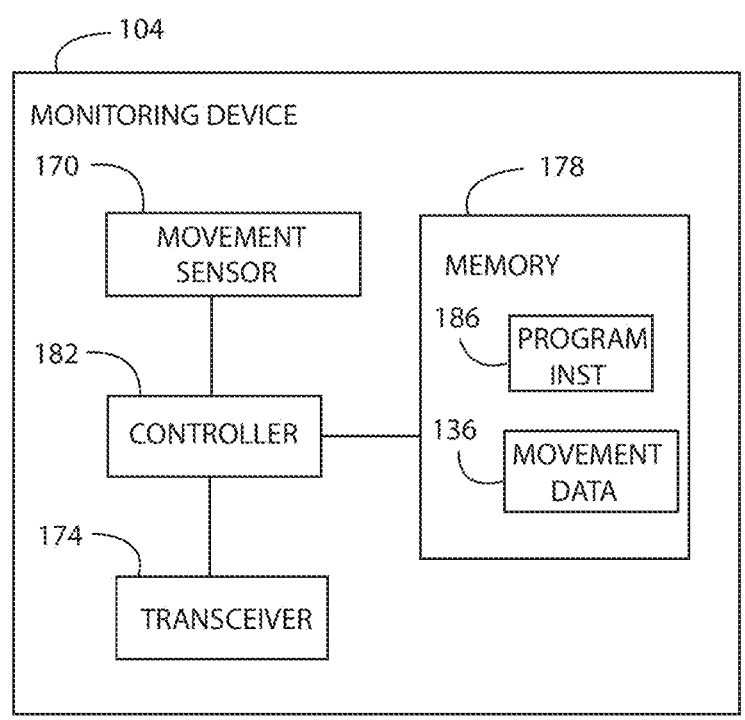
FIG. 2 is a diagram illustrating a monitoring device of the fitness tracking system of FIG. 1.

As shown in FIG. 2, the monitoring device 104, which is also referred to herein as a measuring device, a health parameter monitoring device, a distance monitoring device, a speed monitoring device, and/or an activity monitoring device, includes a movement sensor 170, a transceiver 174, and a memory 178 each of which is operably connected to a controller 182. The movement sensor 170 is configured to collect movement data 136, which corresponds to movement of the user during an exercise session. In one embodiment, the movement sensor 170 is an accelerometer sensor (such as a MEMS accelerometer) and the movement data 136 is (or includes) acceleration data, which corresponds to acceleration of the user during the exercise session. In this embodiment, the movement sensor 170 collects acceleration data that corresponds to bipedal movement of the user. The movement data 136 is stored by the controller 182 in the memory 178. The movement sensor 170 is provided as any type of sensor configured to generate the movement data 136, such as a single-axis or a multi-axis microelectromechanical (MEMS) accelerometer, a gyroscope, and/or a magnetometer.

The transceiver 174 of the monitoring device 104, which is also referred to as a wireless transmitter and/or receiver, is configured to transmit and to receive data from the personal electronic device 108. In one embodiment, the transceiver 174 is configured for operation according to the Bluetooth® wireless data transmission standard. In other embodiments, the transceiver 174 comprises any desired transceiver configured to wirelessly transmit and receive data using a protocol including, but not limited to, Near Field Communication ("NFC"), IEEE 802.11, Global System for Mobiles ("GSM"), and Code Division Multiple Access ("CDMA").

The memory 178 of the monitoring device 104 is an electronic data storage unit, which is also referred to herein as a non-transient computer readable medium. The memory 178 is configured to store the program instruction data 186 and the movement data 136 generated by the movement sensor 170, as well as any other electronic data associated with the fitness tracking system 100, such as user profile information, for example. The program instruction data 186 includes computer executable instructions for operating the monitoring device 104.

The controller 182 of the monitoring device 104 is configured to execute the program instruction data 186 for controlling the movement sensor 170, the transceiver 174, and the memory 178. The controller 182 is a provided as a microprocessor, a processor, or any other type of electronic control chip.

Figure 3:
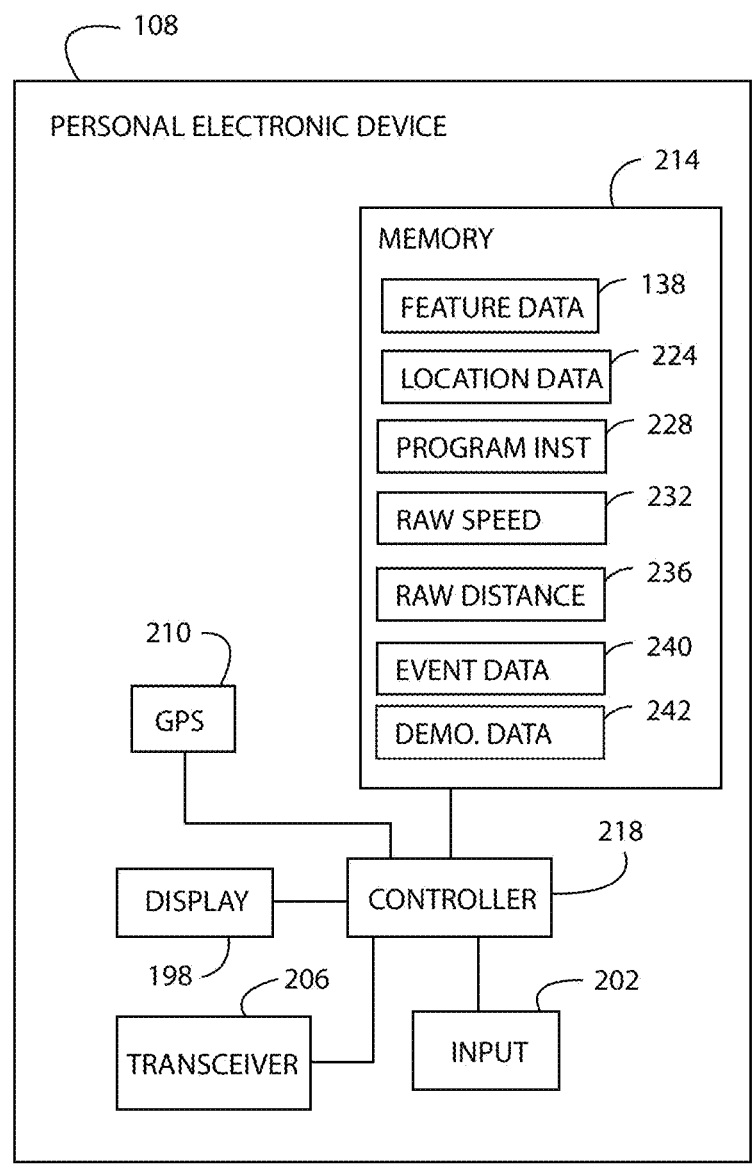
FIG. 3 is a diagram illustrating a personal electronic device of the fitness tracking system of FIG. 1.

As shown in FIG. 3, the exemplary personal electronic device 108 is configured as a smartphone. In other embodiments, the personal electronic device 108 is provided as a smartwatch, an electronic wristband, or the like. In one embodiment, the personal electronic device 108 is configured to be worn or carried by the user during collection of the movement data 136 by the monitoring device 104. In another embodiment, the personal electronic device 108 is not carried or worn by the user during collection of the movement data 136, and the personal electronic device 108 receives the movement data 136 from the monitoring device 104 after the user completes an exercise session. In a further embodiment, data may be transmitted from the monitoring device 104 to the personal electronic device 108 both during and after completion of an exercise session.

The personal electronic device 108 includes display unit 198, an input unit 202, a transceiver 206, a GPS receiver 210, and a memory 214 each of which is operably connected to a processor or a controller 218. The display unit 198 is configured to display a visual representation of the movement variable data 144 (i.e. the estimated speed, distance, stride length, and cadence of the user as determined by the machine learning model 140). The display unit 198 may comprise a liquid crystal display (LCD) panel configured to display static and dynamic text, images, and other visually comprehensible data. For example, the display unit 198 is configurable to display one or more interactive interfaces or display screens to the user including a display of at least an estimated distance traversed by the user, a display of an estimated speed of the user, and a display of an estimated stride length of the user. The display unit 198, in another embodiment, is any display unit as desired by those of ordinary skill in the art.

The input unit 202 of the personal electronic device 108 is configured to receive data input via manipulation by a user. The input unit 202 may be configured as a touchscreen applied to the display unit 198 that is configured to enable a user to input data via the touch of a finger and/or a stylus. In another embodiment, the input unit 202 comprises any device configured to receive user inputs, as may be utilized by those of ordinary skill in the art, including e.g., one or more buttons, switches, keys, and/or the like.

With continued reference to FIG. 3, the transceiver 206 of the personal electronic device 108 is configured to wirelessly communicate with the transceiver 174 of the monitoring device 104 and the remote processing server 112. The transceiver 206 wirelessly communicates with the remote processing server 112 either directly or indirectly via the cellular network 128 (FIG. 1), a wireless local area network ("Wi-Fi"), a personal area network, and/or any other wireless network over the Internet 124. Accordingly, the transceiver 206 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA"). To this end, the transceiver 206 is configured to wirelessly transmit and receive data from the remote processing server 112, and to wirelessly transmit and receive data from the monitoring device 104.

The GPS receiver 210 of the personal electronic device 108 is configured to receive GPS signals from the GPS 132 (FIG. 1). The GPS receiver 210 is further configured to generate location data 224 that is representative of a current location on the Earth of the personal electronic device 108 based on the received GPS signals. The location data 224, in one embodiment, includes latitude and longitude information. The controller 218 is configured to store the location data 224 generated by the GPS receiver 210 in the memory 214.

Figure 6:
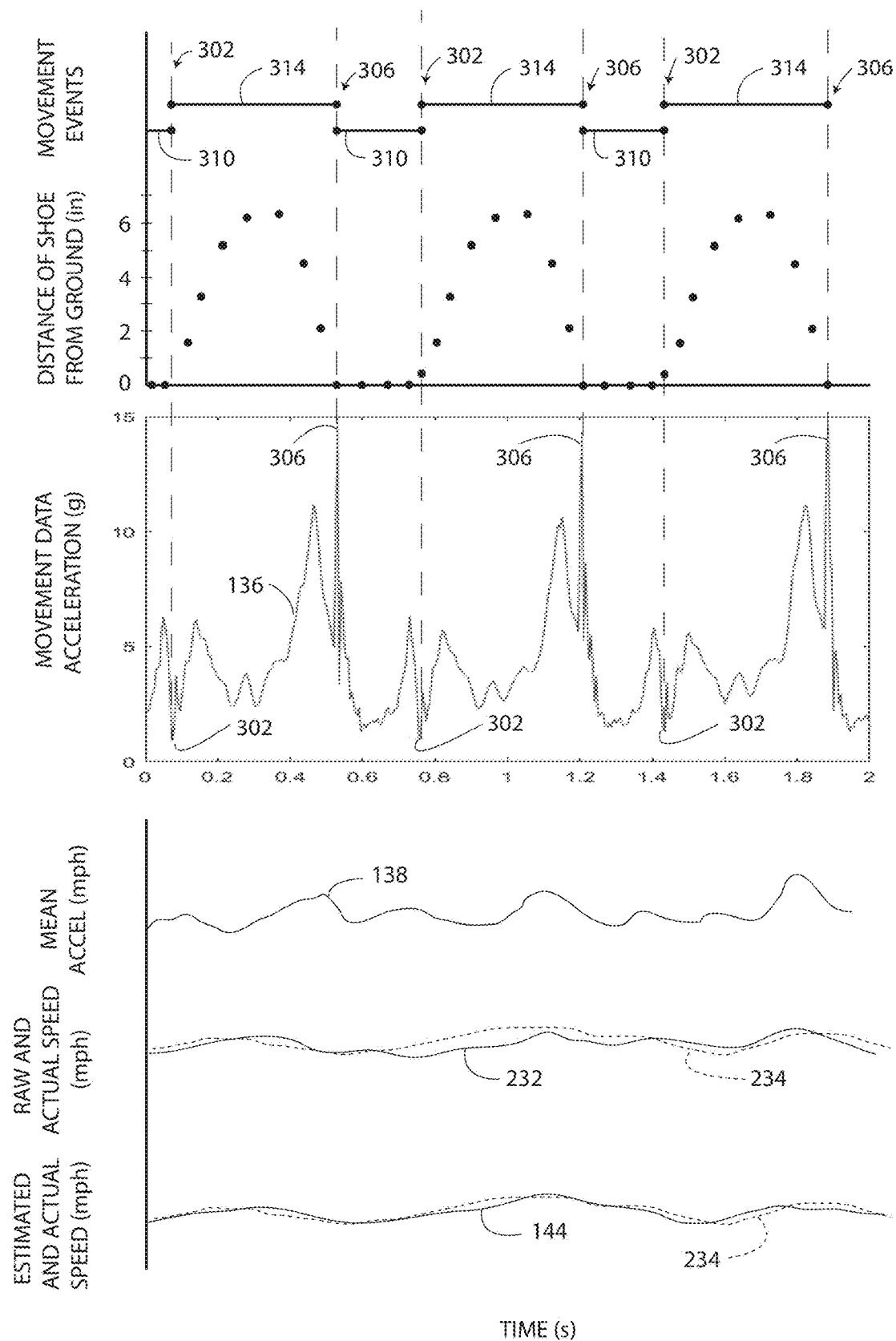
FIG. 6 is a plot of movement event data, foot position, acceleration data, feature data shown as a mean acceleration, raw speed data, and estimated speed data versus time.

As shown in FIG. 3, the memory 214 of the personal electronic device 108 is an electronic data storage unit, which is also referred to herein as a non-transient computer readable medium. The memory 214 is configured to store electronic data associated with operating the personal electronic device 108 and the monitoring device 104 including program instruction data 228, raw speed data 232, raw distance data 236, movement event data 240, demographic data 242, and the feature data 138. The program instruction data 228 includes computer executable instructions for determining the feature data 138, the raw speed data 232, the raw distance data 236, the event data 240, and the demographic data 242. The raw speed data 232 corresponds to a speed of the user that is calculated by the personal electric device 108 based on at least a subset of the movement data 136 collected by monitoring unit 104 during an exercise session. The raw distance data 236 corresponds to a distance traversed by the user that is calculated by the personal electronic device 108 based on at least a subset of the movement data 136 collected by the monitoring unit 104 during an exercise session. The event data 240 corresponds to movement events of the user during the exercise session, such as a takeoff event 302 (FIG. 6), a landing event 306 (FIG. 6), a stance phase event 310 (FIG. 6), and a flight phase event 314 (FIG. 6).

The demographic data 242 is based on demographic information of the user and may include user gender, user height, user weight, user body mass index ("BMI"), and user age, among other data. Any other user demographic and/or psychographic data may be included in the demographic data 242.

The feature data 138 stored in the memory 214 of the personal electronic device 108 corresponds to data calculated by the personal electronic device 108 and/or the monitoring device 104 by applying a set of rules to at least a subset of the movement data 136. In one embodiment, the rules of the set of rules are categorized as mathematical operations, event-specific operations, and processed signals. Exemplary feature data 138 based on the set of rules include mean acceleration, root mean square acceleration, median acceleration, lower quartile acceleration, upper quartile acceleration, an interquartile acceleration range, maximum acceleration, minimum acceleration, a predetermined range of acceleration, standard deviation, variance, complexity, skewness, kurtosis, autocorrelation, a percentage of acceleration data samples above or below the mean acceleration, a percentage of acceleration data samples above the mean acceleration and below the upper quartile acceleration, and a percentage of acceleration data samples below the mean acceleration and above the lower quartile acceleration. Additional feature data 138 based on the set of rules include all statistical moments including, but not limited to, mean (moment ordinal 1), variance (moment ordinal 2), skewness (moment ordinal 3), kurtosis (moment ordinal 4), hyperskewness (moment ordinal 5, and hyperflatness (moment ordinal 6). The feature data 138 include any (or none) of the infinite number of statistical moments. The above rules are exemplary, and the controller 218 and/or the controller 182 are configured to perform at least one rule of the set of rules in calculating the feature data 138 from the movement data 136.

The controller 218 of the personal electronic device 108 is operatively connected to the monitoring device 104 and is configured to execute the program instruction data 228 in order to control the display unit 198, the input unit 202, the transceiver 206, the GPS receiver 210, the memory 214, and the monitoring device 104. The controller 218 is provided as a microprocessor, a processor, or any other type of electronic control chip. The controller 218 is further configured to process at least a subset of the movement data 136 and to calculate the feature data 138 by applying at least one rule of the set of rules to the subset of the movement data 136, for example. Moreover, the controller 218 is configured to calculate the raw speed data 232 and the raw distance data 236 from the subset of the movement data 136 by integrating the subset of the movement data 136, for example. Further, the controller 218 is configured to receive the movement variable data 144 determined by the machine learning model 140 of the remote processing server 112 and to store the movement variable data 144 in the memory 214. In another embodiment, the controller 182 of the monitoring device 104 is configured to execute the program instructions 186 to process at least a subset of the movement data 136 and to calculate the feature data 138 by applying at least one rule of the set of rules to the subset of the movement data 136, for example. Moreover, in this embodiment, the controller 182 is configured to calculate the raw speed data 232 and the raw distance data 236 from the subset of the movement data 136 by integrating the subset of the movement data 136, for example. In another embodiment, the monitoring device 104 is configured to calculate the raw speed data and the raw distance data. Furthermore, in some embodiments, at least one of the personal electronic device 108 and the monitoring device 104 is configured to calculate raw stride length data corresponding to the stride length of the user from the subset of the movement data 136, raw cadence data corresponding to the cadence of the user from the subset of the movement data 136, and raw ground contact time data corresponding to the ground contact time of the user from the subset of the movement data 136. The raw stride length data, the raw cadence data, and the raw ground contact time data are stored in at least one of the memory 178 and the memory 214. The "raw" data may be determined or calculated by one or more of the personal electronic device 108 and the monitoring device 104.

With reference to FIG. 1, the remote processing server 112 is remotely located from the monitoring device 104 and the personal electronic device 108. That is, the server 112 is located in a first physical location and the personal electric device 108 and the monitoring device 104 are located in a second physical location that is different from the first physical location. In a further embodiment, which is discussed in greater detail at FIG. 8, the components of the server 112 are included as part of the personal electronic device 108.

The server 112 is configured to calculate, generate, and/or determine the movement variable data 144 based on at least the feature data 138 calculated, generated, and/or determined by at least one of the personal electronic device 108 and the monitoring device 104. Accordingly, the server 112 is configured to receive the feature data 138, the raw speed data 232, and the raw distance 236 from the personal electric device 108 via the Internet 124. To this end, the server 112 includes a transceiver 252 and a memory 256 storing program instructions 260, the machine learning model 140, and the movement variable data 144. Each of the transceiver 252 and the memory 256 is operably connected to a central processing unit ("CPU") 264.

The movement variable data 144 generated by the machine learning model 140 of the server 112 includes at least one of an estimated speed of the user, an estimated distance traversed by the user, an estimated stride length of the user, an estimated cadence of the user, and an estimated ground contact time of the user's foot/shoe. The estimated speed of the user is an estimated ground speed of the user determined at least periodically during an exercise session monitored by the monitoring device 104. The estimated distance traversed by the user is an estimated distance moved/traversed by the user during the exercise session. The estimated distance is determined accurately when the user utilizes a treadmill, or the like, during the exercise session and is representative of a corresponding distance moved. That is, the user is not required to move a corresponding distance on the ground in order for the machine learning model 140 to determine the estimated distance. The estimated stride length is an estimated heel-to-heel distance of the user determined at least periodically during the exercise session. The estimated cadence of the user is an estimation of the number of steps taken per unit time (e.g. steps per minute) during the exercise session. The estimated ground contact time of the user is an estimation of the time the user's foot is in contact with the ground during each stride of the exercise session.

An advantage of using the machine learning model 140 is that, for example, the estimated speed/distance of the user is a more accurate representation of an actual speed 234 (FIG. 6) and an actual distance of the user than is the raw speed/distance (raw speed data 232 and raw distance data 236) of the user as determined by the personal electronic device 108 or the monitoring device 104. Each "estimated" value of the movement variable data 144 is typically more accurate than the corresponding value (if any) as determined by the personal electronic device 108 or the monitoring device 104.

The transceiver 252 of the remote processing server 112 is configured to wirelessly communicate with the personal electronic device 108 either directly or indirectly via the cellular network 128, a wireless local area network ("Wi-Fi"), a personal area network, and/or any other wireless network. Accordingly, the transceiver 252 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA").

The CPU 264 of the remote processing server 112 is configured to execute the program instruction data 260 stored in the memory 256 for generating and/or determining movement variable data 144 by applying at least one of the feature data 138, the raw speed data 232, the raw distance data 236, the demographic data 242, the raw stride length data, the raw cadence data, and the raw ground contact time data to the machine learning model 140 to generate the movement variable data 144. The CPU 264 is provided as a microprocessor, a processor, or any other type of electronic control chip. Typically, the CPU 264 is more powerful than the controller 218 of the personal electronic device 108, thereby enabling the remote processing server 112 to generate the movement variable data 144 more quickly than the personal electronic device 108.

The machine learning model 140 stored in the memory 256 of the remote processing server 112 in one embodiment, and includes a non-linear neural network regression model to determine the movement variable data 144. In other embodiments, the machine learning model 140 uses other regression models such as multiple linear regression. A single feature datum 138 (such as mean acceleration only) or multiple feature data 138 (such as mean acceleration and root mean square acceleration) may be used as inputs to the machine learning model 140. Moreover, the machine learning model 140 may be implemented in a piecewise manner, and dimensionality reduction, such as principal component analysis ("PCA"), may be used in some embodiments to reduce the complexity of the machine learning model 140.

The machine learning model 140 is trained using training data (i.e. existing feature data and movement variable data) to output data corresponding to the movement variable data 144 (i.e. the estimated speed, distance, stride length, and cadence of the user). As used herein, the term "machine learning model" refers to a system or a set of program instructions configured to implement an algorithm or mathematical model that predicts and provides a desired output based on a given input. In one example, the input is training "feature data" and the desired output is the data corresponding to the movement variable data 144. The machine learning model 140 is typically not explicitly programmed or designed to follow particular rules in order to provide the desired output for a given input. Instead, the machine learning model 140 is provided with the corpus of training data from which the machine learning model 140 identifies or "learns" patterns and statistical relationships or structures in the training data, which are generalized to make predictions with respect to new data inputs (i.e. feature data 138, raw speed data 232, and raw distance data 236 corresponding to "user-generated" movement data 136). In the case of supervised machine learning, the training data is labeled as inputs and outputs, and the machine learning model 140 is trained to predict outputs for new data based on the patterns and other relationships or structures identified in the training data. The training data, however, may also be unlabeled as is the case with unsupervised machine learning. Both training scenarios are suitable for training the machine learning model 140 included in the server 112.

Figure 4:
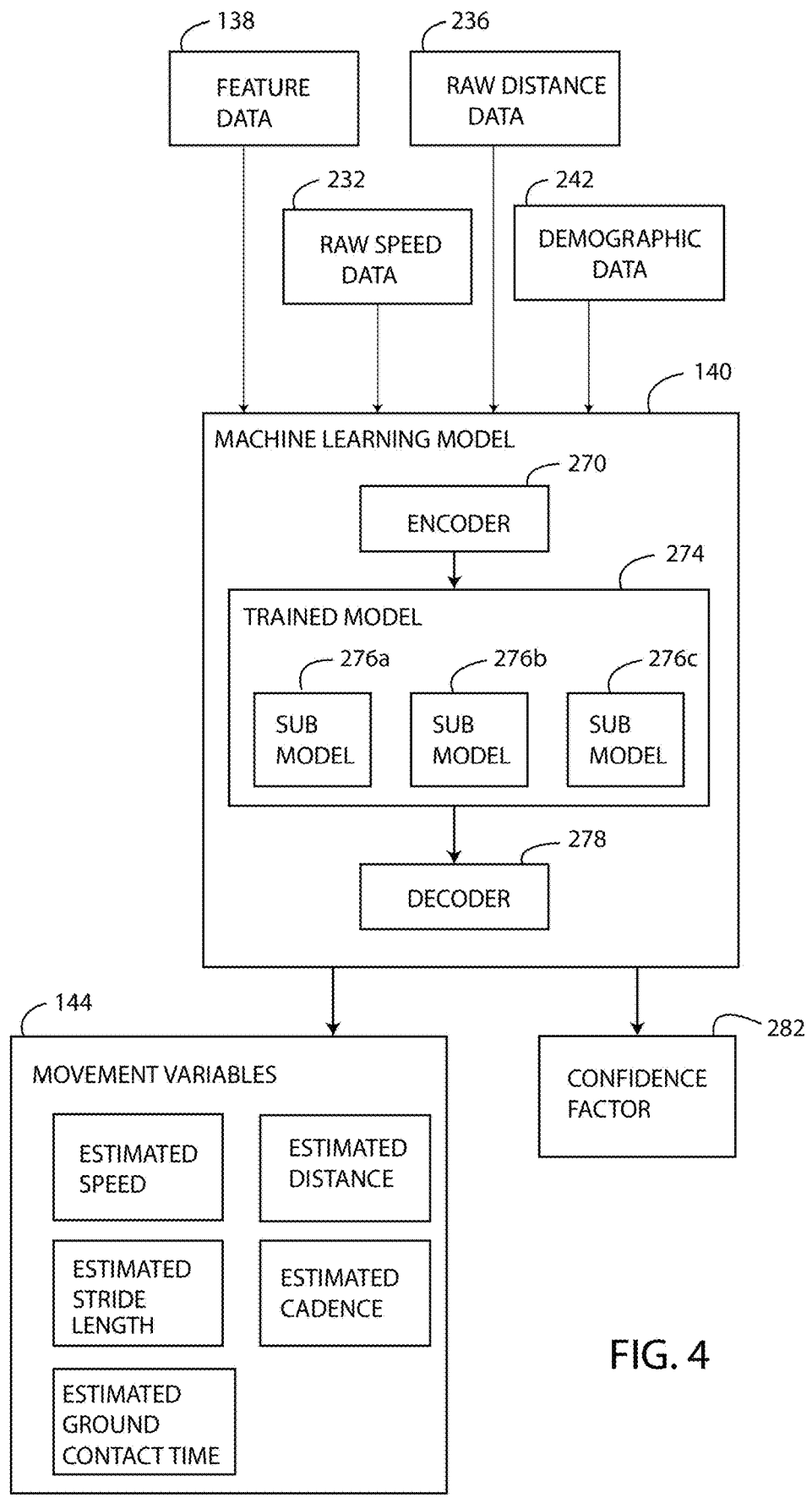
FIG. 4 is a diagram illustrating a machine learning model of the fitness tracking system of FIG. 1.

FIG. 4 illustrates an exemplary simplified block diagram of the logical components of the machine learning model 140 as well as the data that is input to the model 140 and the data that is output from the model 140. The machine learning model 140 includes an encoder 270 operatively connected to a trained model 274, which is operatively connected to a decoder 278. The encoder 270 is configured to reformat the input data (i.e. at least the feature data 138, the raw speed data 232, the raw distance data 236, and the demographic data 242) into a format that is suitable for processing by the trained model 274.

Figure 7:
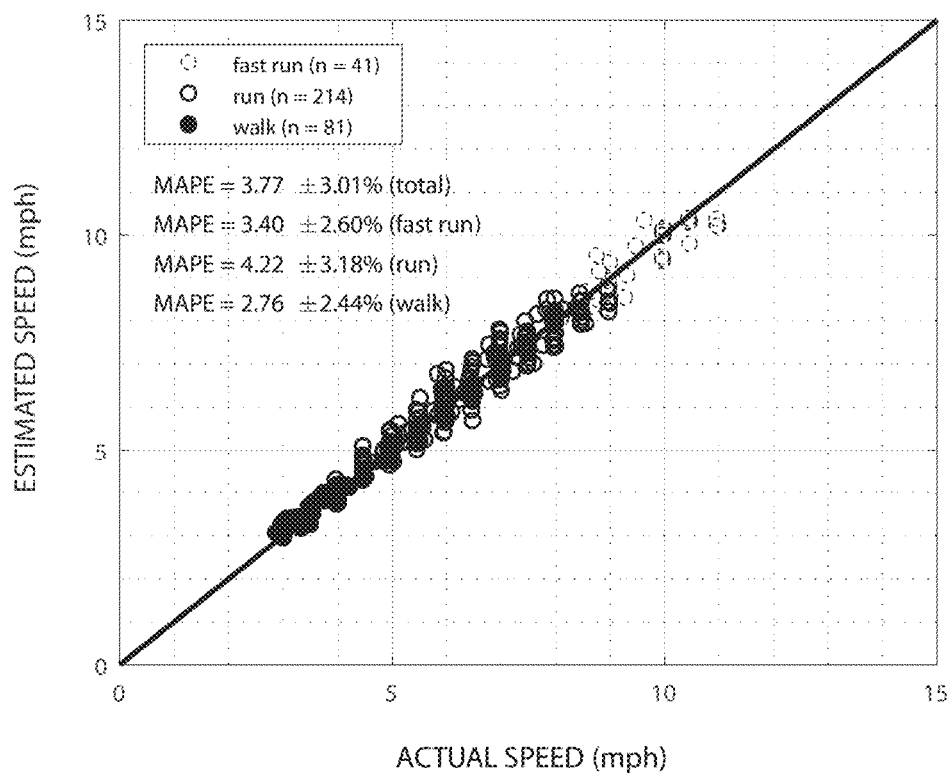
FIG. 7 is a plot of an estimated speed of the user as determined by the fitness tracking system versus an actual speed of the user.

The trained model 274 processes the encoded input data and generates output data. The trained model 274, in at least one embodiment, includes sub-models such as a sub-model 276a, a sub-model 276b, and a sub-model 276c. The trained model 274 includes any number of the sub-models 276a, 276b, 276c. Each of the sub-models 276a, 276b, 276c is configured to receive and process a particular type of input data. For example, in one embodiment, the sub-model 276a is trained to receive feature data 138 that is generated from a walking user, the sub-model 276b is trained to receive feature data 138 that is generated from a running user, and the sub-model 276c is trained to receive feature data 138 that is generated by a fast running user. In an exemplary embodiment, a walking user moves at a speed less than about 4.0 mile per hour ("mph"), a running user moves a speed from 4.0 to 7.0 mph, and a fast running user moves at a speed greater than 7.0 mph. An exemplary output according to the walking/running/fast running model is shown in FIG. 7 and is discussed in detail herein. In another example, the sub-model 276a is trained to receive feature data 138 that is generated from a forefoot-strike mover and is referred to as a forefoot-strike non-linear regression model, the sub-model 276b is trained to receive feature data 138 that is generated from a midfoot-strike mover and is referred to as a midfoot-strike non-linear regression model, and the sub-model 276c is trained to receive feature data 138 that is generated from a heel-strike mover and is referred to as a heel-strike non-linear regression model. The CPU 264 and/or the controller 218 of the personal electronic device 108 is configured to process the movement data 136 and/or the feature data 138 to determine the appropriate sub-model 276a, 276b, 276c (if any) to which the feature data 138 and/or the other input data should be applied. In another embodiment, the trained model 274 does not include the sub-models 276a, 276b, 276c, and the trained model 274 generates the output data for all input data.

The decoder 278 receives the output data from the trained model 274 and reformats the output data into the movement variable data 144 and confidence factor data 282. The confidence factor data 282 is indicative of an accuracy of the determined movement variable data 144. In one embodiment, the confidence factor data 282 is a value from zero to one, but in other embodiments, the confidence factor data 282 includes values within any desired range. Typically, a low confidence factor is associated with less accurately determined movement variable data 144 and a high confidence factor is associated with more accurately determined movement variable 144. The confidence factor data 282 may or may not be stored in the memory 256 of the remote processing server 112.

Figure 5:
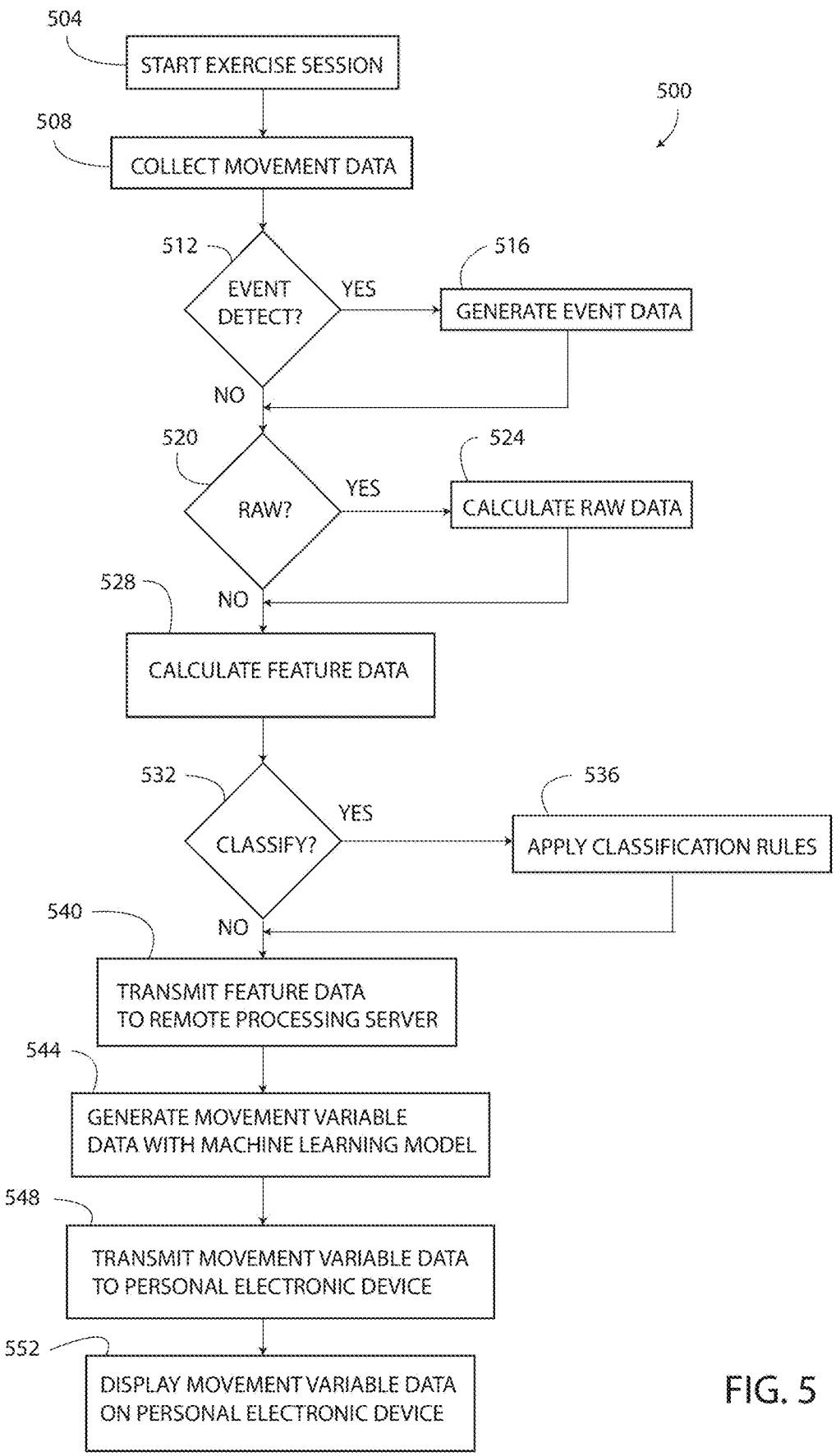
FIG. 5 is a flowchart illustrating a method of operating the fitness tracking system of FIG. 1.

In operation, the fitness tracking system 100 is operated according to a method 500 illustrated by the flowchart of FIG. 5. The fitness tracking system 100 executes the method 500 to determine at least one movement variable (i.e. the movement variable data 144) corresponding to movement of a user wearing or carrying the monitoring device 104 during an exercise session. In block 504, the user engages in an exercise session and wears or carries the monitoring device 104. Specifically, the user runs, walks, or hikes while wearing or carrying the monitoring device 104. Typically, the monitoring device 104 is affixed to the user's shoe 150. The user may also wear or carry the personal electronic device 108; however, the user is not required to wear or carry the personal electronic device 108 during the exercise session.

At block 508, during the exercise session, the monitoring device 104 collects movement data 136 corresponding to, in this exemplary embodiment, the acceleration of the user. Specifically, since the monitoring device 104 is typically affixed to the user's shoe 150, the movement data 136 corresponds to the acceleration of the user's shoe/foot 150 during the exercise session. FIG. 6 includes a plot of exemplary movement data 136 collected by the monitoring device 104 and data corresponding to a distance of the user's shoe 150 from the ground.

Either during the exercise session or at the conclusion of the exercise session, the movement data 136 collected by the monitoring device 104 is wirelessly transmitted to the personal electronic device 108 via the transceivers 174, 206. The personal electronic device 108 stores the movement data 136 in the memory 214.

Next, in block 512, the personal electronic device 108 determines whether the movement data 136 should be processed with movement event detection. Whether or not movement event detection is performed may be specified by the user of the personal electronic device 108 using the input unit 202, or by the program instruction data 238. Movement event detection (or simply "event detection") generates the movement event data 240 (FIG. 3) and associates the movement event data 240 with the feature data 138 and/or the movement data 136. Movement event detection is a processing step that is not required to determine the movement variable data 144, but that tends to increase the accuracy of the movement variable data 144. The movement variable data 144 is accurately determinable without event detection. In other embodiments, the monitoring device 104 determines whether the movement data 136 should be processed with movement event detection.

In block 516, if event detection is to be performed, the personal electronic device 108 detects movement events in the collected movement data 136 and stores the movement event data 240 to the memory 214. Detecting movement events, in one embodiment, includes identifying subsets of the movement data 136 that correspond to the takeoff event 302, the landing event 306, the stance phase event 310, and the flight phase event 314 by processing the movement data 136 with the controller 218 of the personal electronic device 108. In other embodiments, the controller 182 of the monitoring device 104 detects the movement events in the collected movement data 136.

The takeoff event 302, the landing event 306, the stance phase event 310, and the flight phase event 314 are identified in FIG. 6. The takeoff event 302 is indicative of when the user's shoe 150 has left the ground at the beginning of a stride. The landing event 306 is indicative of when the user's shoe 150 has struck the ground at the end of the stride. The flight phase event 314 is located between the takeoff event 302 and the landing event 306. During the flight phase event 314, the user's shoe is spaced apart from the ground and is moving through the air. The stance phase event 310 is located between the landing event 306 and the next takeoff event 302. During the stance phase event 310, the user's shoe 150 is positioned on the ground.

The detected movement events of block 516 are stored as the event data 240 in the memory 214 of the personal electronic device 108 or the memory 104 of the monitoring device 104. In one embodiment, the event data 240 is categorized by event type and includes or identifies subsets of the movement data 136 and/or feature data 138 corresponding to the takeoff event 302, the landing event 306, the stance phase event 310, and the flight phase event 314. As a result, for example, using the event data 240 a subset of the feature data 138 corresponding to only the flight phase event 314 can be isolated and applied to the machine learning model 140 without applying feature data 138 corresponding to the takeoff event 302, the landing event 306, and the stance phase event 310. The event data 240 for the events identified above may be referred to herein as stance phase data including a subset of the movement data 136 that corresponds to the stance phase event 310, takeoff data including a subset of the movement data 136 that corresponds to the takeoff event 302, flight phase data including a subset of the movement data 136 that corresponds to the flight phase event 314, and landing data including a subset of the movement data 136 that corresponds to the landing event 306.

Continuing to block 520, the personal electronic device 108 determines if the movement data 136 should be processed to calculate at least one of the raw speed data 232 and the raw distance data 236. Whether or not the raw data 232, 236 is calculated may be specified by the user of the personal electronic device 108 using the input unit 202, or by the program instruction data 238. The calculation of the raw data 232, 236 is a processing step that is not required to determine the movement variable data 144, but that tends to increase the accuracy of the movement variable data 144. The movement variable data 144 is accurately determinable without applying the raw data 232, 236 to the machine learning model 140.

In block 524, if the raw data calculation is to be performed, the personal electronic device 108 calculates at least one of the raw speed data 232 and the raw distance data 236 by processing the movement data 136. Specifically, to determine the raw speed data 232, the controller 218 integrates at least a subset of the movement data 136. To determine the raw distance data 236, the controller 218 integrates the raw speed data 232. The raw speed data 232 and the raw distance data 236 are stored in the memory 214 of the personal electronic device 108. Exemplary raw speed data 232 is plotted in FIG. 6. The plotted raw speed data 232 is based on the plotted movement data 136, which is acceleration data. In other embodiments, the controller 182 of the monitoring device 104 calculates the raw data 232, 236 from the movement data 136.

Next, in block 528, the controller 218 of the personal electronic device 108 calculates the feature data 138 by applying at least one rule of the set of rules to at least a subset of the movement data 136. The controller 218 stores the feature data 138 in the memory 214 of the personal electronic device 108. The controller 218 performs any desired mathematical operation on the movement data 136 to generate feature data 138 corresponding to a mean acceleration, a median acceleration, a root mean square acceleration, a maximum acceleration, and/or a minimum acceleration. FIG. 6 includes an exemplary plot of a mean acceleration (i.e. feature data 138) based on the plotted movement data 136, which is acceleration data. In one embodiment, the mean acceleration in FIG. 6 is a moving mean taken over a predetermined time period. Moreover, the controller 218 may perform mathematical operations on the movement data 136 to determine feature data 138 including a complexity calculation, a skewness calculation, a kurtosis calculation, a percentage of acceleration samples above or below the mean acceleration, and an autocorrelation calculation. Still further, the controller 218 may perform mathematical operations on the movement data 136 to determine feature data 138 including a lower quartile calculation, an upper quartile calculation, an interquartile range calculation, a percentage of acceleration samples above or below the mean acceleration, a percentage of acceleration data samples above the mean acceleration and below the upper quartile acceleration calculation, and a percentage of acceleration data samples below the mean acceleration and above the lower quartile acceleration calculation. The controller 218 may apply any rule or set of rules and/or perform any mathematical operating or statistical operation on the movement data 136 in calculating the feature data 138. In another embodiment, the controller 182 of the monitoring device 104 determines and/or calculates the feature data 138.

According to an exemplary embodiment, the controller 218 is configured to calculate the feature data 138 based on and corresponding to the movement data 136 of the movement events detected at block 516 of the method 500. For example, the controller 218 may generate a subset of the feature data 138 based on only the movement data 136 of the flight phase event 314 using the event data 240. Additionally or alternatively, the controller 218 may generate another subset of the feature data 138 based on only the movement data 136 of the takeoff event 302 using the event data 240. The controller 218 is configured to generate the feature data 138 based on the movement data 136 of any detected movement event using the event data 240.

In one embodiment, the controller 218 is further configured to calculate combined features stored as combined feature data. The combined feature data is stored in the memory 214 and is applied to the machine learning model 140 in the same way that the feature data 138 is applied to the machine learning model 140. The combined feature data is included in the feature data 138 in the figures. The combined feature data is based on a combination of the feature data 138. For example, combined feature data is formed by combining a mean acceleration and a root mean square acceleration using principal component analysis techniques. Any other data combination technique or process may be used to generate the combined feature data from the feature data 138 using the controller 218.

Moving to block 532, the personal electronic device 108 determines if the user or the program instruction data 228 requires classification of the feature data 138. Classification of the feature data 138 enables the feature data 138 to be organized into subsets that are each associated with a particular type of user. For example, in one embodiment, the controller 218 classifies the feature data 138 based on the speed of the user during various segments of the exercise session each having a predetermined time period.

In block 536, if classification is to be performed, the controller 218 or the controller 182 applies classification rules to the feature data 138 to classify the feature data 138. The classification rules enable the controller 218 or the controller 182 to categorize the feature data 138 into the desired classification structure. An exemplary classification rule states that the mean acceleration feature data 138 is classified as walking data when a maximum acceleration is less than 70 meters per second squared (70 m/s$^2$), running data when the maximum acceleration is 70 m/s$^2$ to 100 m/s$^2$, and fast running data when the maximum acceleration is greater than 100 m/s$^2$. Another classification rule classifies the feature data 138 according to the manner in which the user's feet strike the ground when running or walking. For example, the controller 218 determines if the feature data 138 originated from movement data 136 corresponding to a heel-strike mover, a midfoot-strike mover, or a forefoot-strike mover using an appropriate metric.

Next, in block 540 data is transmitted from the personal electronic device 108 to the remote processing server 112. The transmission of data is typically performed wirelessly using the cellular network 128, a local area network, and/or the Internet 124. The personal electronic device 108 may transmit any data used to generate the movement variable data 144 to the server 112 including the feature data 138 (including combined feature data, classified feature data 138, and/or feature data 138 based on the event data 240), the raw speed data 232, the raw distance data 236, and the demographic data 242. In some embodiments, at least one of the raw speed data 232, the raw distance data 236, and the demographic data 242 are not generated and are not transmitted to the server 112. In a specific embodiment, only the feature data 138 (without combined feature data, classified feature data 138, and feature data 138 based on the event data 240) is transmitted to the remote processing server 112. That is, in this embodiment, the movement data 136 is not transmitted to the remote processing server 112.

As shown in block 544, the remote processing server 112 generates the movement variable data 144 using the machine learning model 140. The movement variable data 144 includes at least the estimated speed of the user based on the movement data 136, the estimated distance the user has moved/traversed based on the movement data 136, the estimated stride length of the user based on the movement data 136, the estimated cadence of the user based on the movement data 136, and the estimated ground contact time of the user based on the movement data 136, as determined by the machine learning model 140. Depending on the embodiment, at least one of the feature data 138, the raw speed data 232, the raw distance data 236, the demographic data 242, the raw stride length data, the raw cadence data, and the raw ground contact time data are applied to (i.e. processed through) the machine learning model 140 to cause the machine learning model 140 to generate the movement variable data 144, which is stored in the memory 256. Depending on the desired processing demands of the remote processing server 112, only certain data are applied to the machine learning model 140. For example, an approach that generates movement variable data 144 with a suitable level of accuracy applies only the feature data 138 to the machine learning model 140, without event detection (i.e. block 516), without the "raw" data, such as the raw speed data 232 and the raw distance data 236 (i.e. block 524), and without classifying the feature data 138 (i.e. block 536). Such an approach generates the movement variable data 144 based on only the feature data 138 without prior integration of the movement data 136 to determine the raw speed data 232 and the raw distance data 236. That is, the machine learning model 140 determines the estimated speed of the user and the estimated distance moved by the user without the movement data 136 (which in this example includes acceleration data) being integrated by either the personal electronic device 108 or the remote processing server 112.

Another approach for determining the movement variable data 144 is to apply the feature data 138, the raw speed data 232, and the raw distance data 236 only to the machine learning model 140. Such an approach generates the movement variable data 144 including at least the estimated speed of the user and the estimated distance traveled by the user. Since the machine learning model 140 is trained based on feature data 138 from many users, the output of the machine learning model 140 is more accurate than the raw movement variables determined directly from the movement data 136. Specifically, the estimated speed of the user as determined by the machine learning model 140 is a more accurate representation of the actual speed 234 (FIG. 6) of the user than the raw speed data 232, and the estimated distance traveled by the user as determined by the machine learning model 140 is a more accurate representation of the actual distance traveled by the user than the raw distance data 236. Exemplary, estimated speed data 144 as determined by the machine learning model 140 and raw speed data 232 are plotted for comparison in FIG. 6. As shown in FIG. 6, both the raw speed data 232 and the estimated speed data 144 closely approximate the actual speed 234 of the user, but the estimated speed data 144 is a closer approximation because the estimated speed data 144 deviates less from the actual speed 234.

Yet another approach for determining the movement variable data 144 is to apply classified feature data 138 and certain "raw" data to the machine learning model 140. For example, the feature data 138 is classified according to the walking/running/fast-running model, as set forth above. At least one of the classified feature data 138, the raw speed data 232, the raw distance data 236, the raw stride length data, the raw cadence data, and the raw ground contact time data is then applied to only the appropriate sub-model 276a, 276b, 276c of the trained model 274. In a specific example, the feature data 138 is classified as "walking" and the feature data 138 is applied to only the walking sub-model 276a to generate the movement variable data 144. Since the sub-model 276a is specially trained with data from "walking" users, the movement variable data 144 is a particularly accurate representation of the actual movements of the user. To illustrate this point, FIG. 7 plots the estimated speed of the user (i.e. movement variable data 144) versus the actual speed of the user for each of the three speed classifications. In one embodiment, the overall mean absolute percentage error ("MAPE") for a model including the walking, running, and fast running sub-models 276a, 276b, 276c is about 3.77±3.01%. In this embodiment, the MAPE for the walking sub-model 276a is only about 2.76±2.44%, the MAPE for the running sub-model 276b is only about 4.22±3.18%, and the MAPE for the fast running sub-model 276c is only about 3.40±2.60%.

In a similar approach, the feature data 138 is classified according to the heel/midfoot/forefoot strike model, as set forth above. At least one of the classified feature data 138, the raw speed data 232, the raw distance data 236, the raw stride length data, the raw cadence data, and the raw ground contact time data is then applied to only the appropriate sub-model 276a, 276b, 276c of the trained model 274. In a specific example, the feature data 138 is classified as "forefoot-strike" and the feature data 138 (and any "raw" data, if desired) is applied to only the forefoot sub-model 276c to generate the movement variable data 144. Since the sub-model 276c is specially trained with data from "forefoot-strike" users, the movement variable data 144 is a particularly accurate representation of the actual movements of the user. A corresponding approach is taken for feature data 138 classified as "midfoot-strike" and "heel-strike."

Next, in block 548 of FIG. 5, the remote processing server 112 transmits the movement variable data 144 to the personal electronic device 108. The transmission of data 144 is typically performed wirelessly using the cellular network 128, a local area network, and/or the Internet 124.

In block 552, the personal electronic device 108 displays a visual representation of the movement variable data 144 on the display unit 198. For example, at the conclusion of the exercise session, at least one of the estimated speed, estimated distance, estimated stride length, estimated cadence, and estimated ground contact time are displayed on the display unit 198 for review by the user. The movement variable data 144 may also be stored on the server 112 for access by the user and others via the Internet 124.

The fitness tracking system 100 includes specific improvements to computer functionality by improving the manner in which the system 100 generates the movement variable data 144. Known fitness tools locally generate user movement data using an on-board processor. In contrast, in at least one embodiment, the fitness tracking system 100 generates the movement variable data 144 at the server 112, which is remote from the monitoring device 104 and the personal electronic device 108. The remote processing configuration reduces the processing demands of the controller 218 of the personal electronic device 108, thereby reducing the electrical power consumed by the personal electronic device 108. Moreover, the powerful remote processing server 112 generates the movement variable data 144 more quickly than the controller 218 to improve the user experience. Furthermore, storing the machine learning model 140 on the server 112 reduces the capacity requirements of the memory 214 of the personal electronic device 108.

The fitness tracking system 100 and associated computer components disclosed herein function differently than conventional fitness tracking systems. Known processes for determining speed and distance from movement data, such as acceleration data, integrate the movement/acceleration data to determine the speed and then integrate the speed to determine the distance. This approach generates results that are typically insufficiently accurate. For example, the determined speed and distance may be plus or minus 10% of the actual speed and the actual distance traversed by the user. Accordingly, the speed and distance generated according to known processes cannot be relied upon by users as accurate training data, thereby making training and fitness more difficult for the user. Moreover, speed and distance calculations made by known devices are typically inconsistent because they do not account for different modes of exercise (e.g. walking vs. running vs. fast running) or differences in biomechanics (e.g. heel-strike vs. midfoot-strike vs. forefoot-strike). Moreover, known devices typically require event detection in order to determine the speed and distance traversed by the user. Event detection typically increases the complexity of the calculations performed by the conventional fitness tracking system, thereby resulting in increased power consumption and/or increased processing time requirements. Furthermore, conventional fitness tracking systems typically require numerical integration of the movement data, which is sensitive to minor inconsistencies and errors. As a result, users typically become frustrated with known fitness tracking systems and seek other options.

The fitness tracking system 100 disclosed herein is an improvement over conventional fitness tracking systems. Specifically, in one embodiment, the fitness tracking system 100 generates the movement variable data 144 without ever integrating the movement data 136. In this embodiment, only the feature data 138 is applied to the machine learning model 140 to generate the movement variable data 144. The feature data 138 is based on the movement data 136, but does not include integrated movement data 136. Instead, the feature data 138 includes mean acceleration, for example, and the machine learning model 140 generates the estimated speed and the estimated distance (i.e. the movement variable data 144) based on the mean acceleration data (i.e. the feature data 138) without receiving or processing the movement data 136. The movement variable data 144 generated by the fitness tracking system 100 is much more accurate than the data generated by known tracking systems. For example, as shown in FIG. 7, the fitness tracking system 100 improves the accuracy of the speed calculation, which overall is within plus or minus 3.77% of the actual speed of the user, as compared to the accuracy of the speed calculation determined by known fitness tracking systems that is only about plus or minus 10%. Moreover, the fitness tracking system 100 is capable of event detection, but is not required to utilize event detection in order to make accurate predictions or estimates of the movement variables associated with the movement variable data 144.

According to another embodiment of the improved fitness tracking system 100, the personal electronic device 108 determines a raw speed and a raw distance of the user (i.e. the raw speed data 232 and the raw distance data 236) by integrating the movement data 136. Then, the integrated movement data 136 and the feature data 138 are applied to a neural network (i.e. the machine learning model 140) in order to determine an even more accurate representation of the actual speed and the actual distance traversed by the user. Therefore, the fitness tracking system 100 disclosed herein results in more than the performance of well-understood, routine, and conventional activities. Moreover, the fitness tracking system 100 entails an unconventional technological solution to a technological problem. Specifically, the unconventional aspect is the application of the raw speed data 232 and the raw distance data 236 to the machine learning model 140 in order to determine an even more accurate representation of the actual speed and the actual distance of the user. The fitness tracking system 100 requires that the recited computer components operate in an unconventional manner to achieve the above-described improvements in computer functionality.

Figure 8:
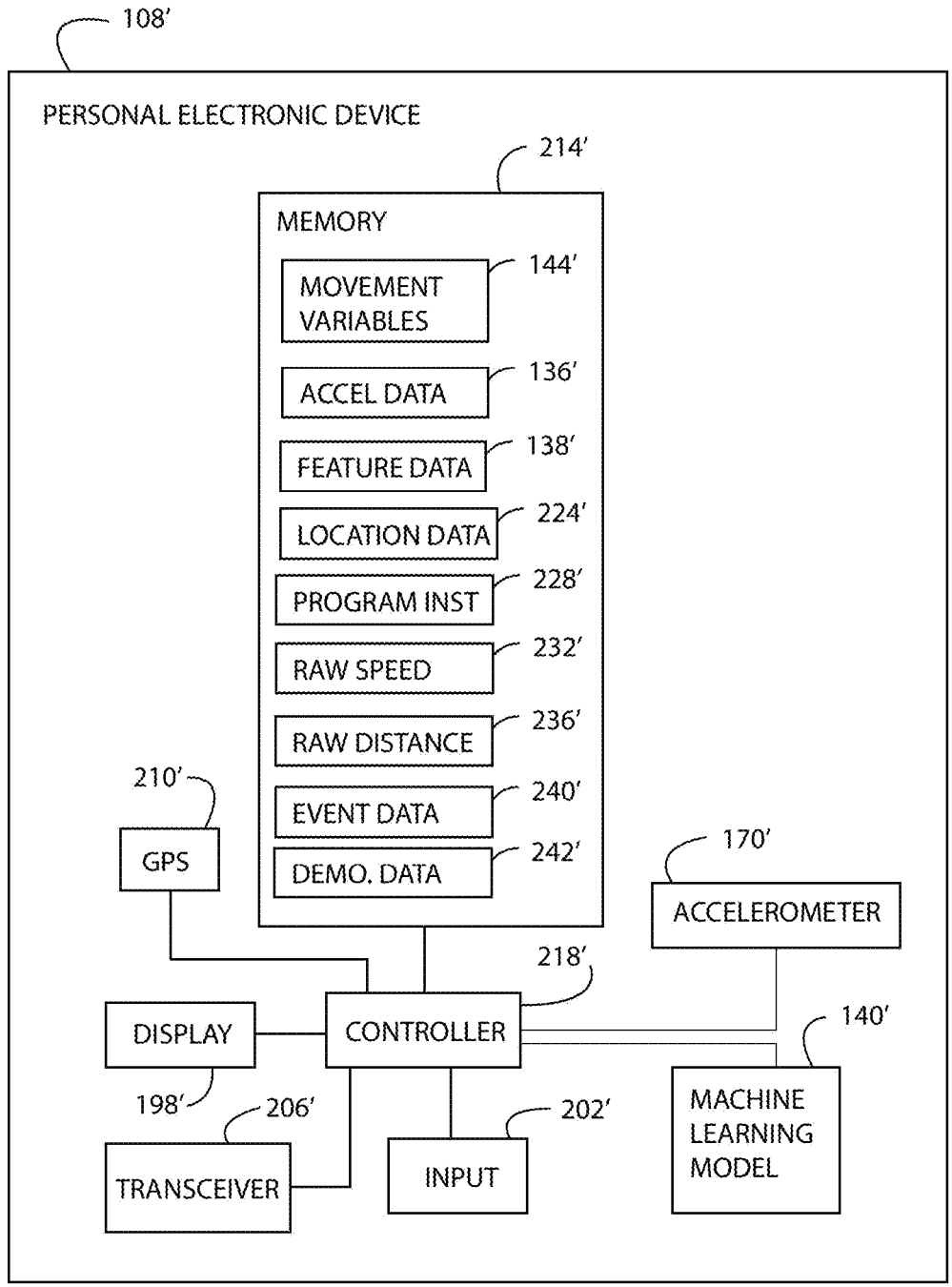
FIG. 8 is a diagram illustrating another embodiment of a personal electronic device as disclosed herein.

As shown in FIG. 8, in another embodiment, a personal electronic device 108' includes a display unit 198', an input unit 202', a transceiver 206', a GPS receiver 210', a memory 214', a movement sensor shown as an accelerometer 170', and a machine learning model 140' each of which is operably connected to a processor or a controller 218'. The memory 214' is configured to store movement data shown as acceleration data 136' collected by the onboard accelerometer 170', feature data 138', raw speed data 232', raw distance data 236', program instruction data 228', location data 224', event data 240', demographic data 242', and movement variable data 144'.

The personal electronic device 108' is substantially the same as the personal electronic device 108 except that the accelerometer 170' (i.e. a movement sensor) is included in the personal electrical device 108' instead of in a separate monitoring device 104. The personal electric device 108' is carried or worn by the user to generate the acceleration data 136' and a separate monitoring device 104 is not required. The personal electronic device 108' also differs from the personal electronic device 108 in that the personal electronic device 108' includes the machine learning model 140'. The personal electronic device 108', therefore, is configured to generate the movement variable data 144' without sending data to a remote processing server 112. The personal electronic device 108' of FIG. 8 is a "self-contained" version of the monitoring device 104, the personal electronic device 108, and the remote processing server 112 of FIG. 1. The personal electronic device 108' is otherwise configured similarly to the personal electronic device 108.

Figure 9:
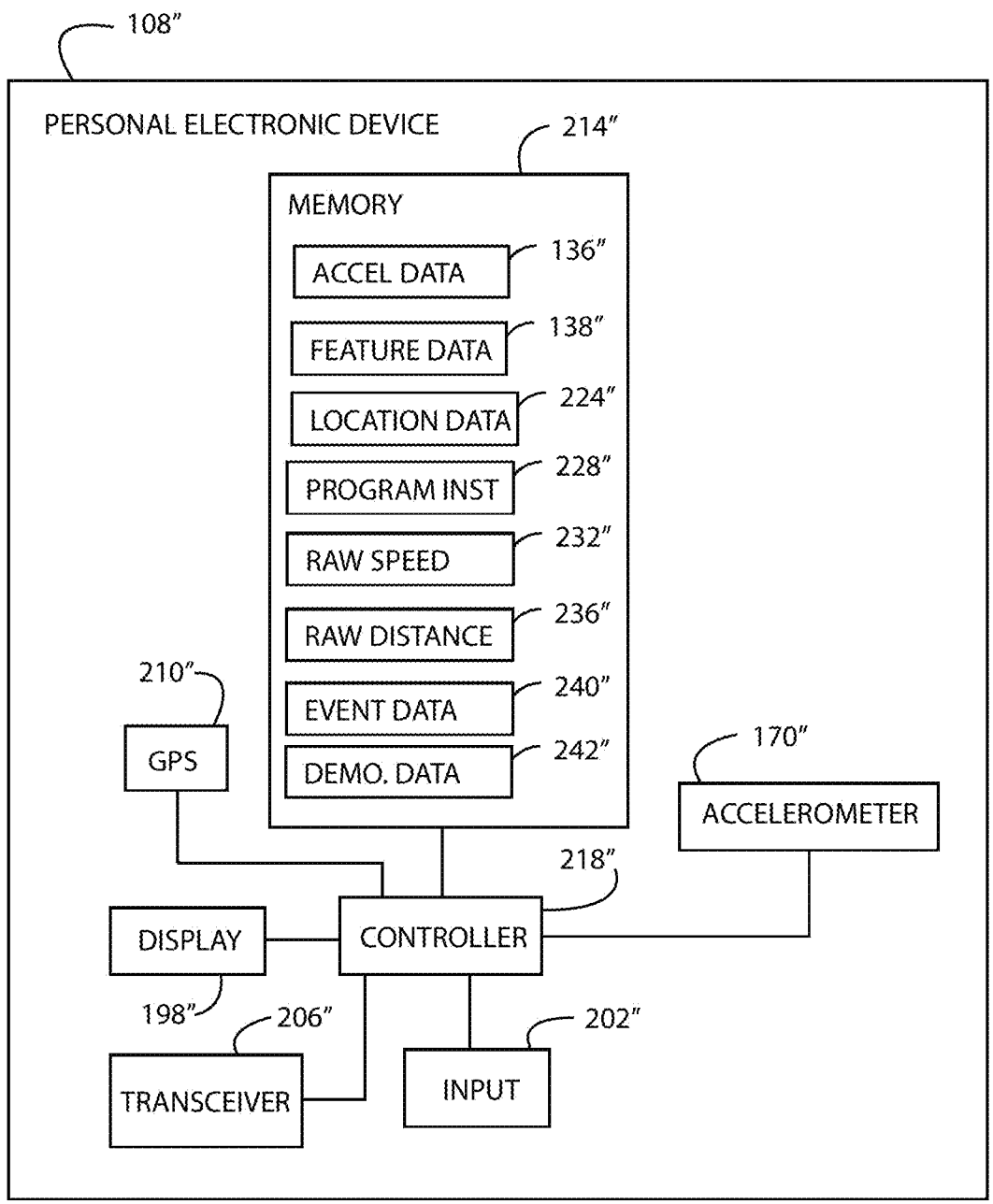
FIG. 9 is a diagram illustrating yet another embodiment of a personal electronic device as disclosed herein.

As shown in FIG. 9, in another embodiment, a personal electronic device 108" includes a display unit 198", an input unit 202", a transceiver 206", a GPS receiver 210", a memory 214", and an accelerometer 170" each of which is operably connected to a processor or a controller 218". The memory 214" is configured to store acceleration data 136" collected by the onboard accelerometer 170", feature data 138", raw speed data 232", raw distance data 236", program instruction data 228", location data 224", event data 240", and demographic data 242".

The personal electronic device 108" is substantially the same as the personal electronic device 108 except that the accelerometer 170" is included in the personal electrical device 108" instead of in a separate monitoring device 104. The personal electric device 108" is carried or worn by the user to generate the acceleration data 136" and a separate monitoring device 104 is not required. The personal electronic device 108", sends feature data 138" to the remote server 112 (FIG. 1) for generation of the movement variable data 144 (FIG. 1). The personal electronic device 108" is otherwise configured similarly to the personal electronic device 108.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

It will be appreciated that the foregoing aspects of the present disclosure, or any parts or functions thereof, may be implemented using hardware, software, firmware, tangible non-transitory computer readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A fitness tracking system for generating at least one movement variable corresponding to movement of a user, the fitness tracking system comprising:
a remote processing server in communication with a personal electronic device, the remote processing server comprising a machine learning model, the remote processing server configured to receive from the personal electronic device movement data corresponding to movement of a user, raw speed data corresponding to a speed of the user, raw distance data corresponding to a distance moved by the user, and feature data calculated by applying a set of rules to the movement data, the remote processing server further configured to apply the machine learning model to the feature data, the raw speed data, and the raw distance data to determine movement variable data corresponding to the at least one movement variable,
wherein the at least one movement variable comprises at least one of an estimated speed of the user, an estimated distance moved by the user, and an estimated stride length of the user, and
wherein the remote processing service is configured to transmit to the personal electronic device the at least one movement variable determined by the machine learning model of the remote processing server.

2. The fitness tracking system of claim 1 further comprising a monitoring device configured to be worn or carried by the user and comprising a movement sensor configured to collect the movement data corresponding to movement of the user.

3. The fitness tracking system of claim 2 wherein the personal electronic device or the monitoring device is configured to calculate the feature data by applying the set of rules to a subset of the movement data, to calculate the raw speed data corresponding to a speed of the user from the subset of the movement data, and to calculate the raw distance data corresponding to a distance moved by the user from the subset of the movement data.

4. The fitness tracking system of claim 1, wherein:
the machine learning model is a neural network regression model,
the remote processing server configured to receive from the personal electronic device at least one of raw stride length data corresponding to a stride length of the user from a subset of the movement data, raw cadence data corresponding to a cadence of the user from the subset of the movement data, and raw ground contact time data corresponding to a ground contact time of the user from the subset of the movement data,
the movement data includes acceleration data corresponding to an acceleration of the user,
the feature data comprises at least one of a mean acceleration, a median acceleration, a root mean square acceleration, a maximum acceleration, a minimum acceleration,
the remote processing server is further configured to apply the machine learning model to at least one of the raw stride length data, the raw cadence data, and the raw ground contact time data to determine the movement variable data, and
the at least one movement variable further comprises at least one of an estimated cadence of the user and an estimated ground contact time of the user.

5. The fitness tracking system of claim 1, wherein the personal electronic device further comprises:
a display unit operably connected to the controller, the display unit configured to display a visual representation of the movement variable data, and
wherein the transceiver of the personal electronic device is configured to wirelessly transmit the feature data to the remote processing server, to wirelessly receive the movement variable data from the remote processing server, and to wirelessly receive the movement data from the monitoring device.

6. The fitness tracking system of claim 1, wherein:
the monitoring device is permanently embedded in a sole of a shoe worn by the user, and
the personal electronic device is worn or carried by the user during the collection of the movement data.

7. A method of operating a fitness tracking system by determining at least one movement variable corresponding to movement of a user associated with a personal electronic device, the method comprising:
receiving feature data from the personal electronic device, the feature data calculated by applying a set of rules to movement data collected by the personal electronic device;
receiving raw speed data from the personal electronic device, the raw speed data corresponding to a speed of the user;
receiving raw distance data from the personal electronic device, the raw distance data corresponding to a distance moved by the user;
applying at least the feature data, the raw speed data, and the raw distance data to a machine learning model at a remote processing server to determine movement variable data corresponding to the at least one movement variable, the at least one movement variable comprising at least one of an estimated speed of the user, an estimated distance moved by the user, and an estimated stride length of the user; and
transmitting the movement variable data to the personal electronic device with the remote processing server.

8. The method of claim 7 further comprising:
displaying a visual representation of the movement variable data on a display of the personal electronic device,
wherein the estimated speed of the user is a more accurate representation of an actual speed of the user than the raw speed data, and
wherein the estimated distance moved by the user is a more accurate representation of an actual distance moved by the user than the raw distance data.

9. The method of claim 7, wherein:
the machine learning model comprises a neural network regression model,
the movement data includes acceleration data corresponding to an acceleration of the user,
the feature data comprises at least one of a mean acceleration, a median acceleration, a root mean square acceleration, a maximum acceleration, and a minimum acceleration, and
the method further comprises:
receiving from the personal electronic device at least one of raw stride length data corresponding to a stride length of the user from the movement data, raw cadence data corresponding to a cadence of the user from the movement data, and raw ground contact time data corresponding to a ground contact time of the user from the movement data; and
applying at least one of the raw stride length data, the raw cadence data, and the raw ground contact time data to the machine learning model to determine the movement variable data, the at least one movement variable further comprising at least one of an estimated cadence of the user and an estimated ground contact time of the user.

10. The method of claim 9, wherein the detected movement event corresponds to a stride of the user comprising a stance phase event, a takeoff event, a flight phase event, and a landing event, and the method further comprises:
receiving, from at least one of the monitoring device and the personal electronic device, at least one of stance phase data of the subset of the movement data that corresponds to the stance phase event, takeoff data of the subset of the movement data that corresponds to the takeoff event, flight phase data of the subset of the movement data that corresponds to the flight phase event, and landing data of the subset of the movement data that corresponds to the landing event; and
calculating the feature data based on and corresponding to at least one of the stance phase data, the takeoff data, the flight phase data, and the landing data.

11. The method of claim 7, further comprising:
identifying demographic data corresponding to the user, the demographic data comprising at least one of gender data, height data, weight data, body mass index data, and age data; and
applying at least the demographic data to the machine learning model to determine the movement variable data.

12. The method of claim 7, wherein the set of rules comprises at least one of a complexity calculation, a skewness calculation, a kurtosis calculation, a percentage of acceleration data samples above or below a mean acceleration, and an autocorrelation calculation.

13. The method of claim 7, wherein:
the movement data includes acceleration data corresponding to an acceleration of the user, and
the set of rules comprises at least one of a lower quartile acceleration calculation, an upper quartile acceleration calculation, an interquartile acceleration range calculation, a percentage of acceleration data samples above or below a mean acceleration, a percentage of acceleration data samples above the mean acceleration and below the upper quartile acceleration calculation, and a percentage of acceleration data samples below the mean acceleration and above the lower quartile acceleration calculation.

14. The method of claim 7, wherein:
the machine learning model comprises a heel-strike non-linear regression model, a midfoot strike non-linear regression model, and a forefoot strike non-linear regression model,
the movement data includes acceleration data corresponding to an acceleration of the user, and
the method further comprises:
calculating, with at least one of the monitoring device and the controller of the personal electronic device, at least one of raw stride length data corresponding to a stride length of the user from the subset of the movement data, raw cadence data corresponding to a cadence of the user from the subset of the movement data, and raw ground contact time data corresponding to a ground contact time of the user from the subset of the movement data;
determining if the subset of the acceleration data corresponds to a heel-strike stride of the user, a midfoot-strike stride of the user, or a forefoot-strike stride of the user;
applying at least the feature data, the raw speed data, the raw distance data, the raw stride length data, the raw cadence data, and the raw ground contact time data to only the heel-strike non-linear regression model to determine the movement variable data, if the subset of the acceleration data corresponds to the heel-strike stride;
applying at least the feature data, the raw speed data, the raw distance data, the raw stride length data, the raw cadence data, and the raw ground contact time data to only the midfoot-strike non-linear regression model to determine the movement variable data, if the subset of the acceleration data corresponds to the midfoot-strike stride; and
applying at least the feature data, the raw speed data, the raw distance data, the raw stride length data, the raw cadence data, and the raw ground contact time data to only the forefoot-strike non-linear regression model to determine the movement variable data, if the subset of the acceleration data corresponds to the forefoot-strike stride.

15. The method of claim 7 wherein the movement data is first collected by a monitoring device operably connected to the personal electronic device, the method further comprising:
detecting a movement event with at least one of the monitoring device and the personal electronic device, wherein a subset of the movement data corresponds to the detected movement event.

16. A method for calculating at least one of a speed of a user and a distance traversed by a user with a fitness tracking system, comprising:
collecting movement data corresponding to movement of the user at a personal electronic device worn or carried by the user;
calculating feature data by applying a set of rules to at least a subset of the movement data collected by the personal electronic device;
wirelessly transmitting the feature data from the personal electronic device to a remote processing server, wherein the remote processing server comprises a machine learning model;
receiving, at the personal electronic device, movement variable data from the remote processing server, the movement variable data calculated by the machine learning model based on the feature data and corresponding to the at least one movement variable, the at least one movement variable including at least one of the speed of the user and the distance traversed by the user; and
displaying a visual representation of the movement variable data on the display unit of the personal electronic device.

17. The method of claim 16, wherein:
the machine learning model comprises a neural network regression model,
the movement data includes acceleration data corresponding to an acceleration of the user,
the feature data comprises at least one of a mean acceleration, a median acceleration, a root mean square acceleration, a maximum acceleration, and a minimum acceleration, and
the method further comprises
receiving, at the personal electronic device, at least one of raw stride length data corresponding to a stride length of the user from the subset of the movement data, raw cadence data corresponding to a cadence of the user from the subset of the movement data, and raw ground contact time data corresponding to a ground contact time of the user from the subset of the movement data, wherein at least one of the raw stride length data, the raw cadence data, and the raw ground contact time data are applied to the machine learning model to determine the movement variable data, the at least one movement variable further comprising at least one of an estimated cadence of the user and an estimated ground contact time of the user.

18. The method of claim 16, wherein:

the movement data includes acceleration data corresponding to an acceleration of the user, and the set of rules comprises at least one of a complexity calculation, a skewness calculation, a kurtosis calculation, a percentage of acceleration data samples above or below a mean acceleration, and an autocorrelation calculation.

19. The method of claim 16, wherein:

the movement data includes acceleration data corresponding to an acceleration of the user, and the set of rules comprises at least one of a lower quartile acceleration calculation, an upper quartile acceleration calculation, an interquartile acceleration range calculation, a percentage of acceleration data samples above or below a mean acceleration calculation, a percentage of acceleration data samples above the mean acceleration and below the upper quartile acceleration calculation, and a percentage of acceleration data samples below the mean acceleration and above the lower quartile acceleration calculation.

20. The method of claim 16, further comprising:

calculating combined feature data, at the personal electronic device, based on a combination of a subset of the calculated feature data; and wirelessly transmitting the combined feature data from the personal electronic device to the remote processing server; and wherein the movement variable data is calculated based in part on the combined feature data.

21. The method of claim 20, wherein the combined feature data is calculated using at least principal component analysis.

* * * * *